Figure 1:
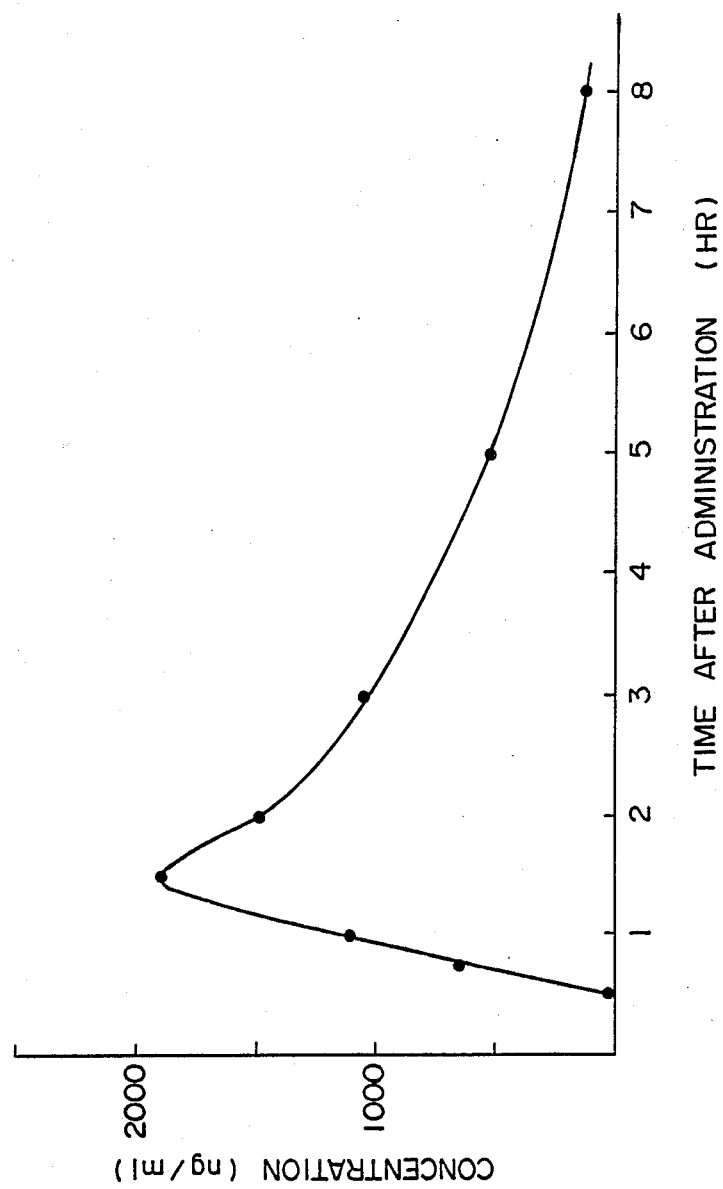

United States Patent [19]

Suzuki et al.

[11] Patent Number: 4,910,216
[45] Date of Patent: * Mar. 20, 1990

[54] 2-(3,5-DIMETHYL-4-HYDROXYPHENYL)INDOLE DERIVATIVES

[75] Inventors: Yasushi Suzuki, Yokohama; Yukio Hasegawa, Yamato; Michitaka Sato, Kawasaki; Morinobu Saito, Kawasaki; Norio Yamamoto, Kawasaki; Katsuhiko Miyasaka, Atsugi; Takashi Mikami, Yokohama; Katsuhiko Miyazawa, Kawasaki, all of Japan

[73] Assignee: Teikoku Hormone Mfg. Co., Ltd., Tokyo, Japan

[*] Notice: The portion of the term of this patent subsequent to Sep. 22, 2004 has been disclaimed.

[21] Appl. No.: 160,281

[22] Filed: Feb. 25, 1988

[51] Int. Cl.[4] .................. C07D 209/18; A61K 31/405
[52] U.S. Cl. ...................................... 514/415; 548/511
[58] Field of Search ........................ 548/511; 514/415

[56] References Cited

U.S. PATENT DOCUMENTS 4,695,581  9/1987  Suzuki .............................. 514/415
4,708,964  11/1987  Allen ............................... 514/533

FOREIGN PATENT DOCUMENTS 0162573  9/1983  Japan .
2053962  3/1987  Japan .

Primary Examiner—Mukund J. Shah
Assistant Examiner—Frederick F. Tsung
Attorney, Agent, or Firm—Wenderoth, Lind & Ponack

[57] ABSTRACT

A compound of the formula

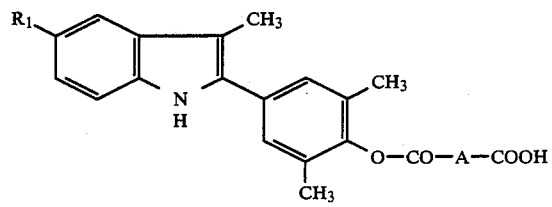

wherein $R_1$ is a hydrogen atom or a methoxy group, and A is a $C_1$-$C_4$ alkylene group, or a pharmaceutically acceptable salt thereof. This compound is useful as a medicine, particularly as a lipoxygenase inhibitor for polyunsaturated fatty acids.

5 Claims, 1 Drawing Sheet

2-(3,5-DIMETHYL-4-HYDROXYPHENYL)INDOLE DERIVATIVES

This invention relates to novel 2-(3,5-dimethyl-4-hydroxyphenyl)indole derivatives, and more specifically, to compounds of the formula

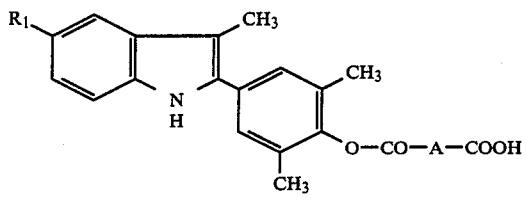

wherein $R_1$ is a hydrogen atom or a methoxy group, and A is a $C_1-C_4$ alkylene group, or a pharmaceutically acceptable salt thereof, a process for production thereof, and the use thereof as a medicine, particularly as a lipoxygenase inhibitor for polyunsaturated fatty acids.

A polyunsaturated fatty acid, typically arachidonic acid, is a constituent of phospholipids present in a biological membrane, and by various stimulations such as an inflammation-inducing stimulation or an antigen-antibody reaction (immunological stimulation), is liberated from the biological membrane into the cells. The liberated arachidonic acid is usually metabolized by cyclooxygenase and lipoxygenase. A slow reacting substance of anaphylaxis [composed of a mixture of leukotriene $C_4$ ($LTC_4$), leukotriene $D_4$ ($LTD_4$) and leukotriene $E_4$ ($LTE_4$)) formed by metabolization of arachidonic acid by 5-lipoxygenase is considered to be one of the important substances which participate in an allergic reaction and cause an allergic symptom. Peroxidized fatty acids, products of metabolization of polyunsaturated fatty acids by lipoxygenase, exert biologically deleterious effects; for example, they inhibit the formation of prostacyclin which plays an important role in the defense of a biological tissue.

Heretofore, 3-amino-1-(3-trifluoromethylphenyl)-2-pyrazoline [BW755C] and 5,8,11,14-eicosatetraynoic acid, for example, have been known as lipoxygenase inhibitors. These compounds, however, lack specificity and inhibit not only lipoxygenase but also cyclooxygenase.

The present inventors previously found that certain novel 2-(3,5-dialkyl-4-hydroxyphenyl)indole derivatives have an excellent action of inhibiting lipoxygenase for polyunsaturated fatty acids, and filed an application for patent on an invention relating to this finding (European Patent Application Publication No. 173,279 and U.S. Pat. No. 4,695,581). These indole derivatives show good lipoxygenase-inhibiting activity in oral administration to rats. It has now been found in accordance with this invention that compounds represented by formula (I) given above show stronger lipoxygenase-inhibiting activity and surprisingly, much higher bioavailability.

In formula (I), the $C_1-C_4$ alkylene group may be linear or branched, and includes, for example, methylene, ethylene, propylene, methylethylene, butylene, and 2-methylpropylene. The $C_2$ or $C_3$ alkylene groups are especially preferred.

Typical examples of the compounds of formula (1) provided by this invention are as follows:

2-4-(3-carboxypropionyloxy)-3,5-dimethylphenyl]-5-methoxy-3-methylindole,
2-4-(3-carboxypropionyloxy)-3,5-dimethylphenyl]-3-methylindole,
2-4-(4-carboxybutyryloxy)-3,5-dimethylphenyl]-5-methoxy-3-methylindole,
2-4-(4-carboxybutyryloxy)-3,5-dimethylphenyl]-3-methylindole,
2-4-(5-carboxyvaleryloxy)-3,5-dimethylphenyl]-5-methoxy-3-methylindole,
2-4((4-carboxy-3-methylbutyryloxy)-3,5-dimethylphenyl]-5-methoxy-3-methylindole, and
2-4-(2-carboxyacetyloxy)-3,5-dimethylphenyl]-5-methoxy-3-methylindole.

Compounds of formula (I) in which $R_1$ is a methoxy group and A is an ethylene or propylene group are preferred. Especially preferred are those of formula (I) in which $R_1$ is a methoxy group and A is an ethylene group.

The compounds of formula (I) can exist as salts, for example salts with metals such as sodium or potassium.

According to this invention, the compounds of formula (I) can be produced by reacting a compound of the formula

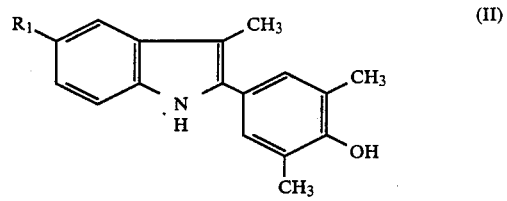

wherein $R_1$ is as defined above, with a lower alkanoic acid anhydride of the formula

wherein A is as defined above.

The reaction of the compound of formula (II) with the lower alkanoic acid anhydride of formula (III) can be carried out, for example, (i) in a basic organic solvent such as pyridine, dimethylaniline, quinoline or triethylamine, or a mixture of the basic organic solvent with another solvent such as toluene, xylene, tetralin, dimethylformamide or dimethoxyethane at a temperature of generally 50° C. to the refluxing temperature of the reaction mixture, preferably 90° C. to the refluxing temperature of the reaction mixture, or (ii) in the presence of a base such as sodium hydride, potassium hydride or sodiumamide in a solvent such as dimethylformamide or diethylformamide at a temperature of usually −20° C. to room temperature, preferably 0° C. to room temperature.

The amount of the compound of formula (III) to be used relative to the compound of formula (II) is not particularly limited. Generally, it is advantageous to use 1 to 2 moles, preferably about 1.1 to 1.3 moles, of the compound of formula (III) per mole of the compound of formula (II). It is sufficient that in the reaction under the reaction conditions described in (ii), the base is used in an amount of about 1 to 1.2 moles per mole of the compound of formula (II).

The compound of formula (I) so obtained may be isolated from the reaction mixture and purified by methods known per se such as extraction, filtration, distillation, recrystallization and chromatography.

The compound of formula (II) used as the starting material in the above reaction is described in the above-cited European Patent Application Publication No. 173,279 and U.S. Pat. No. 4,695,81.

As required, the compound of formula (I) produced by the process described above can be converted into its salt. This can be carried out in a manner known per se by treating it with an inorganic base in the absence of solvent or in a suitable inert solvent by a conventional method.

The compounds of formula (I) provided by the present invention have the activity of inhibiting the formation of lipoxygenase metabolites by selectively inhibiting the lipoxygenase particularly 5-lipoxygenase, for polyunsaturated fatty acids present in biological membranes. Accordingly, the compounds of formula (I) provided by this invention are useful for inhibiting physiological and pathological activities which are induced by the lipoxygenase metabolites and are biologically undesirable.

In particular, the compounds provided by this invention are characterized by showing very good absorption in oral administration.

More specifically, the compounds of formula (I) provided by this invention can be used as an anti-asthma agent, an antiallergic agent (for the prevention and treatment of allergic dermatitis, allergic rhinitis, urticaria, gastrointestinal tract allergy, food allergy and other allergic diseases), an anti-rheumatic agent, an antithrombotic agent, an agent for treating arteriosclerosis, an agent for treating vasospasm following subarachnoid hemorrhage, an agent for treating impaired cerebral circulation, an agent for treating coronary insufficiency, an agent for treating ischemic myocardial infarction, an agent for treating ischemic cerebral infarction, an agent for treating ischemic mucosal injury of the gastrointestinal tract, and agent for treating disseminated intravascular coagulation syndrome, an agent for regulating immunity, an agent for treating ulcerative colitis, and an agent for treating psoriasis.

The following animal experiments demonstrate that the compounds of formula (I) have the activity of inhibiting lipoxygenase for polyunsaturated fatty acids.

(1) Preparation of $A_{23187}$-induced pleurisy

Under ether anaesthesia, 0.2 ml of 100 $\mu$M $A_{21187}$ (prepared by adding injectable distilled water in a 2mM $A_{23187}$ ethanol solution) was administered intrapleurally to rats (Wistar-strain, male, 11 weeks old). Twenty minutes after the administration, the rats were exsanguinated and the pleural exudate was harvested. The test compound was suspended or dissolved in a 0.5% carboxymethyl cellulose solution containing 2% Tween, and orally administered to the animals 60 minutes before the intrapleural administration of $A_{23187}$.

(2) Measurement of the leukotrienes [$LTC_4$, $LTD_4$ and $LTE_4$]

To the exudate obtained in (1) was added 4 times its volume of ice-cooled ethanol. They were well mixed, and then centrifuged. The supernatant was concentrated under reduced pressure, and 1.0 ml of 0.01M acetate buffer (pH 5.9) was added to the residue. The solution was added to SEP-PAK ® ($C_{18}$) and leukotrienes were partially purified. Fractions eluted with 5 ml of 60% ethanol/0.01M acetate buffer (pH 5.9) were collected, and the solvent was evaporated under reduced pressure.

The residue was dissolved in 1 ml of methanol, and the solution was filtered on a filter having a pore size of 0.45 microns, and evaporated under reduced pressure. The residue was dissolved in the mobile phase (acetonitrile/water/acetic acid/triethylamine, 35/63.5/1.5/2.2) used in high performance liquid chromatography (HPLC) and subjected to analysis by HPLC. A calibration curve was obtained by a fixed amount of $PGB_2$ as an internal standard substance and standard $LTC_4$, $LTD_4$ and $LTE_4$ were added to a buffer, followed by the same extraction, partial purification and HPLC analysis as above. The amounts of the leukotrienes in the sample were calculated from the calibration curve.

The results are tabulated below. The activity of 2-(4-hydroxy-3,5-dimethylphenyl)-5-methoxy-3-methylindole (compound A) which is disclosed in Example 1 of U.S. Pat. No. 4,695,381 and was selected as an active control is also shown below.

| Compound | dose (mg/kg, p.o.) | $LTC_4 + LTD_4 + LTE_4$ (ng) |
|---|---|---|
| Vehicle | — | 414.82 ± 49.81 |
| Compound of Example 1 | 3 | 193.30 ± 28.37 (53.4) |
| Compound A | 3 | 282.10 ± 35/93 (32.0) |

Each value represents mean ± S.E.M.
Figures in parentheses indicate percent inhibition.

Measurement of the Concentration of the Compound of the Invention in Blood in Oral Administration Male beagle dogs weighing 7 to 13 kg, 5 per group, were used as experimental animals. The compound obtained in Example 1 was filled in a capsule in an amount of 35.54, $\mu$mole/kg. The capsule was orally administered to the animals and immediately then, 50 ml of water was injected into the stomach through a catheter. The blood was drawn from the animals 0.25, 0.5, 0.75, 1, 1., 2, 3, 5, 8, 12, and 24 hours after the administration. After mixing with sodium heparin, plasma samples were prepared in a customary manner. The plasma concentration was measured by using HPLC (column: $\mu$Bondapak ® $C_{18}$).

The results are shown in the attached drawing, FIG. 1.

The compound of formula (I) provided by this invention can be administered orally, parenterally (for example, intramuscularly, intravenously, subcutaneously, or intrarectally), or topically to man and other mammals for the treatment or prevention of various diseases induced by the participation of lipoxygenase metabolites.

For use as medicaments, the compound of formula (I) may be formulated into various forms suitable for oral, parenteral or topical administration. For example, the compound of this invention can be formulated by using various nontoxic carriers or diluents normally used in drugs of this type, for example, vehicles, binders, lubricants, disintegrants, antiseptics, isotonizing agents, stabilizers, dispersants, antioxidants, coloring agents, flavoring agents, buffers, propellants and surface-active agents.

Depending upon their uses, such medicaments may be formulated into tablets, capsules, granules, powders, pellets, pills, trouches, suppositories, ointments, patchss, injectable preparations, syrups, and aerosols. Specific examples of the nontoxic carriers or diluents which can be used include starch, gelatin, glucose, lactose, fructose, maltose, magnesium carbonate, talc, magnesium stearate, methyl cellulose, carboxymethyl cellulose or its salts, gum arabic, polyethylene glycol, alkyl p-hydroxybenzoates, syrup, ethanol, propylene glycol, Vaseline, carbowax, glycerol, sodium chloride, sodium sulfite, sodium phosphate, citric acid, dichlorodifluoromethane, 1,2-dichlorotetrafluoroethane and sorbitan trioleate.

The medicaments may also contain other therapeutically effective drugs.

The dose of the compound of formula (I) can be varied widely depending upon the type of the animal to be treated, the route of administration, the severity of the condition, the diagnosis of a physician, etc. Generally, it may be 0.2 to 20 mg/kg, preferably 0.4 to 10 mg/kg, per day. It is of course possible to administer the compound of formula (I) in a dose larger than the above-specified upper limit or smaller than the above-specified lower limit according to the severity of the patient's condition and the physician's diagnosis. The above dose may be taken once a day or in several divided portions a day.

The following examples further illustrate the present invention.

EXAMPLE 1

In 30 ml of dry dimethylformamide was dissolved 0.88 g of 60% sodium hydride in oil. With ice cooling and stirring, a solution of 5.62 g of 2-(4-hydroxy-3,5-dimethylphenyl)-5-methoxy-3-methylindole in dry dimethylformamide was added dropwise. After the addition, the mixture was stirred further for 1 hour. A solution of 2.2 g of succinic anhydride in dimethylformamide was added dropwise to the resulting solution. After the addition, the mixture was stirred at room temperature for 2 hours, then heated at 50° C. for 30 minutes, and further stirred at room temperature for 3 hours. The reaction solution was poured into water, acidified with dilute hydrochloric acid, and extracted with ethyl acetate. The organic layer was washed with water, and extracted with aqueous sodium bicarbonate solution. The extracted aqueous layer was acidified with dilute hydrochloric acid, and extracted with 100 ml of ethyl acetate three times. The organic layers were washed and dried, and the solvent was evaporated under reduced pressure to give a crystalline residue. Rerrystallization of the residue from ethyl acetate/benzene gave 2-4-(3-carboxy- propionyloxy)-3,5-dimethylphenyl]-5-methoxy-3-methylindole.

Melting point 136.1°–137.3° C.

NMR,$\delta$ppm, $(CD_3)_2SO$: 2.18 (6H, s), 2.38 (3H, s), 2.4–3.1 (4H, m), 3.76 (3H, s), 6.7 (1H, q, J=9 Hz, 3 Hz), 6.94 (1H, d, J=3 Hz), 7.21 (1H, d, J=9 Hz), 7.35 (2H, s), 10.81 (1H).

EXAMPLE 2

In 100 ml of dry dimethylformamide was dissolved 2.4 g of 60% sodium hydride in oil, and with ice cooling and stirring, 15 g of crystals of 2-(4-hydroxy-3,5-dimethylphenyl)-3-methylindole was added little by little. The mixture was further stirred for 1 hour. With ice cooling and stirring, a solution of 6 g of succinic anhydride in dimethylformamide was added dropwise to this solution. After the addition, the mixture was stirred further at room temperature for 5 hours. The reaction solution was poured into water, acidified with dilute hydrochloric acid, and extracted with ethyl acetate. The organic layer was washed with water, and then extracted with 200 ml of saturated aqueous sodium bicarbonate solution three times. The extracts were washed with 100 ml of ethyl acetate twice. The sodium bicarbonate aqueous layer was acidified with dilute hydrochloric acid and xtracted with 200 ml of ethyl acetate twice. The organic layers were washed with water and dried. The solvent was evaporated under reduced pressure, whereupon the residue crystallized. The residue was recrystallized from ethyl acetate/benzene to 9give 2-[4-(3-carboxypropionyloxy)-3,5-dimethylphenyl -3-methylindole.

Melting point: 144.7°–145.7° C.

NMR, $\delta$ppm $(CD_3)_2SO$: 2.2 (6H, s), 2.4 (3H, s), 2.3–3.1 (4H, m), 6.9–7.7 (4H, m), 7.38 (2H, s), 11.02 (1H).

EXAMPLE 3

Glutaric anhydride and 2- 4-hydroxy-3,5-dimethylphenyl)-5-methoxy-3-methylindole were treated in the same way as in Example 1 to give 2-4-(4-carboxybutyryloxy)-3,5-dimethylphenyl]-5-methoxy-3-methylindole.

Melting point: 125°–129° C.

NMR, $\delta$ppm, $CDCl_3$: 2.18 (6H, s), 2.37 (3H, s), 2.05–2.82 (6H, m), 3.87 (3H, s), 6.84 (1H, q, J=8 Hz, 2 Hz), 7.05 (1H, d, J=2 Hz), 7.17 (2H, s), 7.19 (1H, d, J=8 Hz), 7.80 (1 H, s), 10.76 (1H, s).

EXAMPLE 4

In the same way as in Example 1, 2-(4-hydroxy-3,5-dimethylphenyl)-5-methoxy-3-methylindole and 3-methylpentanedioic anhydride were treated to give 2-4-(4-carboxy-3-methylbutyryloxy)-3,5-dimethylphenyl-5-methoxy-3-methylindole.

Melting point: 124°–128° C.

NMR, $\delta$ppm, $CDCl_3$: 1.19 (3H, d), 2.12(6H, s), 2.35 (3H, s), 1.8–2.85 (5H, m), 3.86 (3H, s), 6.83 (1H, q, J=8 Hz, 2 Hz), 7.00 (1H, d, J=2 Hz), 7.13 (2H, s), 7.18 (1H, d, J=8 Hz), 7.80 (1H, s), 10.35 (1H, s).

EXAMPLE 5

This example illustrates the formulation of a drug containing the compound of formula (I) provided by this invention.

| Recipe 1-a for 50 mg capsules | |
|---|---|
| | mg/capsule |
| Active ingredient | 50 |
| Starch | 20 |
| Lactose | 28 |
| Carboxymethyl cellulose | 10 |
| Magnesium stearate | 2 |
| | 110 mg |

| Recipe 1-b for 100 mg capsules | |
|---|---|
| | mg/capsule |
| Active ingredient | 100 |
| Starch | 40 |
| Lactose | 56 |
| Carboxymethyl cellulose | 20 |
| Magnesium stearate | 4 |
| | 220 mg |

The active ingredient was well crushed, and mixed with starch, lactose, carboxymethyl cellulose and magnesium stearate. After thorough mixing, the mixture was filled in capsules.

What is claimed is:

1. A compound of the formula

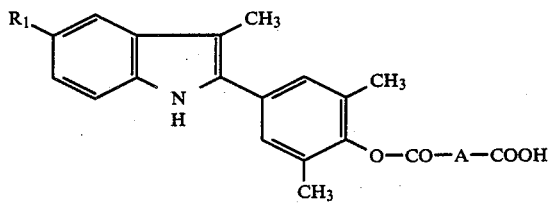

wherein $R_1$ is a hydrogen atom or a methoxy group, and A is a $C_1$–$C_4$ alkylene group, or a pharmaceutically acceptable salt thereof.

2. The compound of claim 1 wherein $R_1$ is a methoxy group and A is an ethylene or propylene group.

3. The compound of claim 1 which is 2-[4-(3-carboxypropionyloxy)-3,5-dimethylphenyl]-5-methoxy-3-methylindole.

4. A pharmaceutical composition for inhibiting 5-lipoxygenase comprising a 5-lipoxygenase inhibiting amount of a compound defined in claim 1 or its pharmaceutically acceptable salt in combination with a pharmaceutically acceptable carrier or diluent.

5. A method of treating a mammal suffering from a condition induced by a 5-lipoxygenase metabolite selected from the group consisting of asthma, an allergic disease, an ischemic myocardial infarction and ischemic cerebral infarction, which comprises administering a 5-lipoxygenase inhibiting amount of a compound defined in claim 1 or its pharmaceutically acceptable salt to the mammal.

* * * * *